US012766314B2

(12) United States Patent
Vrabec et al.

(10) Patent No.: US 12,766,314 B2
(45) Date of Patent: Oct. 20, 2026

(54) SYSTEM FOR ACCELERATED RECOVERY FROM DIRECT CURRENT (DC) NERVE BLOCK USING REPOLARIZATION

(71) Applicant: Case Western Reserve University, Cleveland, OH (US)

(72) Inventors: Tina L. Vrabec, Cleveland, OH (US); Kevin L. Kilgore, Cleveland, OH (US); Jesse S. Wainright, Cleveland, OH (US); Niloy Bhadra, Cleveland, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 565 days.

(21) Appl. No.: 17/437,873

(22) PCT Filed: Mar. 13, 2020

(86) PCT No.: PCT/US2020/022583

§ 371 (c)(1),
(2) Date: Sep. 10, 2021

(87) PCT Pub. No.: WO2020/190694

PCT Pub. Date: Sep. 24, 2020

(65) Prior Publication Data

US 2022/0168563 A1 Jun. 2, 2022

Related U.S. Application Data

(60) Provisional application No. 62/818,773, filed on Mar. 15, 2019.

(51) Int. Cl.
*A61N 1/20* (2006.01)

(52) U.S. Cl.
CPC .................................... *A61N 1/205* (2013.01)

(58) Field of Classification Search
CPC ......... A61N 1/205; A61N 1/20; A61N 1/0551
See application file for complete search history.

(56) References Cited

U.S. PATENT DOCUMENTS 5,755,750 A * 5/1998 Petruska .............. A61N 1/0551 607/118
9,625,387 B2 4/2017 Demos et al.
(Continued)

FOREIGN PATENT DOCUMENTS

WO 2013188753 A1 12/2013
WO 2017044542 A1 3/2017
(Continued)

OTHER PUBLICATIONS

European Search Report for corresponding Application No. 23194830. 8,-1126 dated Aug. 12, 2023, pp. 1-8.
(Continued)

*Primary Examiner* — Mark W. Bockelman
(74) *Attorney, Agent, or Firm* — DINSMORE & SHOHL LLP

(57) ABSTRACT

Accelerated recovery from direct current (DC) nerve block can be achieved using repolarization. A direct current (DC) waveform can be applied to a nerve for a time sufficient to achieve nerve block. The DC waveform can be switched to another DC waveform of reversed polarity, which can be applied for a second time, causing the nerve to enter a repolarization cycle to accelerate recovery time for the nerve. Moreover, simply applying a subthreshold DC waveform to the nerve for a time by itself can enhance a response of the nerve without blocking conduction in the nerve.

13 Claims, 4 Drawing Sheets

(56) References Cited

U.S. PATENT DOCUMENTS

| | | | |
|---|---|---|---|
| 9,964,489 B2 | 5/2018 | Levenson et al. | |
| 2016/0101286 A1* | 4/2016 | Bhadra ................ | A61N 1/3615 607/46 |
| 2017/0050024 A1 | 2/2017 | Bhadra et al. | |
| 2018/0028691 A1 | 2/2018 | Feuerstein | |
| 2018/0214689 A1 | 8/2018 | Zhang et al. | |
| 2018/0280691 A1 | 10/2018 | Ackermann et al. | |

FOREIGN PATENT DOCUMENTS

| | | |
|---|---|---|
| WO | 2017062272 A1 | 4/2017 |
| WO | 2018075473 A1 | 4/2018 |

OTHER PUBLICATIONS

Woods V Met al: "Offset prediction for charge-balanced stimulus waveforms;Offset prediction for charge-balanced stimulus waveforms", Journal of Neural Engineering, Institute of Physics Publishing, Bristol, GB, vol. 8, No. 4, Jul. 13, 2011 (Jul. 13, 2011), p. 46032, XP020209277, ISSN: 1741-2552, DOI: 10.1088/1741-2560/8/4/046032.

Gareau, Daniel S. "Feasibility of digitally stained multimodal confocal mosaics to simulate histopathology." Journal of biomedical optics 14.3 (2009): 034050.

Han, Jefferson Y. "Low-cost multi-touch sensing through frustrated total internal reflection." Proceedings of the 18th annual ACM symposium on User interface software and technology. 2005.

Switz, Neil A., Michael V. D'Ambrosio, and Daniel A. Fletcher. "Low-cost mobile phone microscopy with a reversed mobile phone camera lens." PloS one 9.5 (2014): e95330.

International Search Report for corresponding Serial No. 2020022583, dated Jul. 7, 2020.

Niloy Bhadra et al: "Reversible conduction block in peripheral nerve using electrical waveforms", Bioelectronics in Medicine, vol. 1, No. 1, Jan. 1, 2018 (Jan. 1, 2018) , pp. 39-54, XP055564049, ISSN: 2059-1500, DOI: 10.2217/bem-2017-0004.

Vrabec Tina et al: "Continuous Direct Current Nerve Block Using Multi Contact High Capacitance Electrodes", IEEE Transactions on Neural Systems and Rehabilitation Engineering, IEEE, USA, vol. 25, No. 6, Jun. 1, 2017 (Jun. 1, 2017), pp. 517-529, XP011653663, ISSN: 1534-4320, DOI: 10.1109/TNSRE.2016.2589541 [retrieved on Jun. 20, 2017].

European search report dated Feb. 12, 2025 for Application No./Patent No. 25193156.4-1122/4653042, 9 pages.

* cited by examiner

SYSTEM FOR ACCELERATED RECOVERY FROM DIRECT CURRENT (DC) NERVE BLOCK USING REPOLARIZATION

RELATED APPLICATIONS

This application claims priority to U.S. Provisional Application Ser. No. 62/818,773, filed Mar. 15, 2019, entitled "ACCELERATED RECOVERY OF DC BLOCKING USING REPOLARIZATION". The entirety of this provisional application is hereby incorporated by reference for all purposes.

GOVERNMENT SUPPORT

This invention was made with U.S. government support under 1R01-NS-074149 awarded by the National Institutes of Health, National Institute of Neurological Disease and Stroke (NIH NINDS), as well as R01-EB-002091 and R01-EB-024860 awarded by the National Institutes of Health, National Institute of Biomedical Imaging and Bioengineering (NIH NIBIB). The government has certain rights in this invention.

TECHNICAL FIELD

The present disclosure relates generally to electrical block of transmission of neural signals and, more specifically, to accelerated recovery from direct current (DC) nerve block and/or enhancing condition using repolarization.

BACKGROUND

Direct current (DC) can be applied to a nerve to generate a complete nerve block. Using conventional electrodes (e.g., platinum electrodes), however, applying DC to a nerve can lead to the generation of irreversible reaction products that can damage the nerve. New electrodes, such as the separated interface nerve electrode (SINE), have been developed that are designed to reduce or eliminate the damaging effects of the irreversible reaction products when the DC is applied to the nerve. For example, the SINE can separate the electrode from the nerve using a biocompatible, ionically conducting medium, which isolates the damaging reactions in a vessel away from the nerve. However, when the DC is applied to the nerve to achieve complete block for a prolonged period of time using the new electrodes, a delay is seen in the reversibility of the block and recovery of the neural response, requiring a substantial recovery period. In many cases, it would be advantageous for the recovery period to be reduced so that neural response to be restored more quickly.

SUMMARY

The present disclosure provides a way to reduce the recovery period so that neural response (e.g., conduction) is restored more quickly after application of a direct current (DC) to block conduction in the nerve for a prolonged period of time. By applying a DC of an opposite polarity with a sub-threshold amplitude, neural response can be restored and/or enhanced.

In an aspect, the present disclosure can include a system that can accelerate recovery time in a nerve. The system can include a current generator configured to generate a DC with an amplitude for a time and to generate another DC with another amplitude for another time. The other amplitude has a reverse polarity from the amplitude. The system can also include an electrode, coupled to the current generator and configured to apply the DC to a nerve to block conduction in the nerve for a time and apply the other DC to the nerve for the other time. Application of the other DC causes the nerve to enter a repolarization cycle to accelerate recovery time for the nerve.

In another aspect, the present disclosure can include a method for accelerating the recovery of nerve conduction. The steps of the method can include: blocking conduction in a nerve by applying a DC waveform to the nerve for a time; and switching from the DC waveform to another DC waveform of reversed polarity to enter a repolarization cycle to accelerate recovery time for the nerve for a second time. The DC waveform of reversed polarity can be of a subthreshold amplitude.

In still another aspect, the present disclosure can include a method for enhancing a response of the nerve without blocking conduction in the nerve. The method can include the application of a cathodic or anodic DC waveform with a subthreshold amplitude to a nerve for a time to enhance a response of the nerve without blocking conduction in the nerve. The subthreshold DC waveform is applied to the nerve for the time by itself (with no other electrical waveforms).

BRIEF DESCRIPTION OF THE DRAWINGS

The foregoing and other features of the present disclosure will become apparent to those skilled in the art to which the present disclosure relates upon reading the following description with reference to the accompanying drawings, in which.

DETAILED DESCRIPTION

I. Definitions

Figure 1:
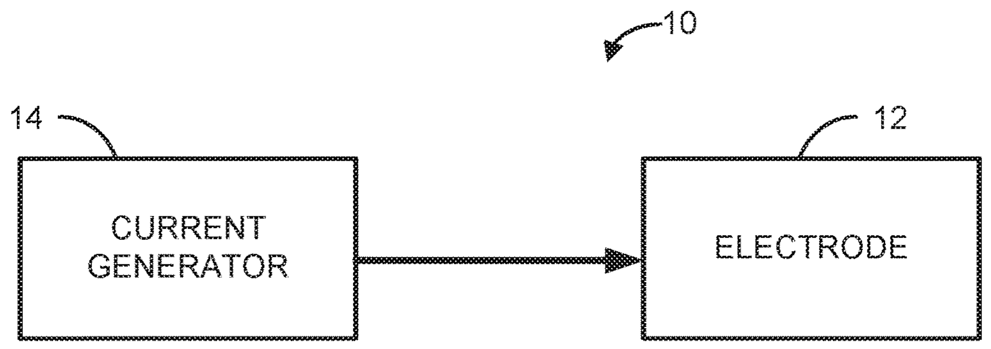
FIG. 1 is a schematic diagram showing an example of a system that can be used to achieve accelerated recovery from direct current (DC) nerve block using repolarization in accordance with an aspect of the present disclosure.

Unless otherwise defined, all technical terms used herein have the same meaning as commonly understood by one of ordinary skill in the art to which the present disclosure pertains.

As used herein, the singular forms "a," "an" and "the" can also include the plural forms, unless the context clearly indicates otherwise.

As used herein, the terms "comprises" and/or "comprising," can specify the presence of stated features, steps, operations, elements, and/or components, but do not preclude the presence or addition of one or more other features, steps, operations, elements, components, and/or groups.

As used herein, the term "and/or" can include any and all combinations of one or more of the associated listed items.

As used herein, the terms "first," "second," etc. should not limit the elements being described by these terms. These terms are only used to distinguish one element from another. Thus, a "first" element discussed below could also be termed a "second" element without departing from the teachings of the present disclosure. The sequence of operations (or acts/steps) is not limited to the order presented in the claims or figures unless specifically indicated otherwise.

As used herein, the terms "electrical block", "electrical nerve block", "nerve conduction block", and "nerve block" (as well as variations thereof) can refer to the attenuation of conduction in one or more nerves within target neural tissue by a purposeful interference with nerve activation. The interference with nerve activation can be due to a change in the electric field caused by application of an electrical signal (to the neural tissue. Attenuating conduction can refer to extinguishing 100% (complete block) or less (partial block) (e.g., 90%, 80%, 70%, 60%, 50%, or the like) of the action potentials traveling through the target neural tissue. In some instances, the electrical block can be can be partial or complete and reversible. The electrical block can be a "hyperpolarization block" or a "depolarization block".

As used herein, the term "electrical signal" can refer to a time-varying voltage or current. As an example, the electrical signal can transmit a direct current (DC). For example, "DC block" can refer to the application of a DC pulse with an amplitude and polarity configured to cause a change in electric field (to depolarize or hyperpolarize) sufficient to alter conduction in the nerve.

As used herein, the term "direct correct (DC)" can refer to a type of electrical signal that includes a unidirectional flow of electric charge (e.g., varying in time, not amplitude). For example, the DC can have a plateau of a cathodic polarity or an anodic polarity. However, in some instances, at least a portion of the amplitude may vary—for example, the DC can further be represented as a waveform that includes a ramp from a zero position to the plateau and may also include a ramp down from the plateau position to the zero position. As another example, the waveform can include a subsequent plateau of the opposite polarity (in such cases, the waveform can be a biphasic waveform with the second phase configured to reduce charge either as a charge balanced waveform or a charge imbalanced waveform). The waveform can also include ramps from zero to the plateau and/or from the plateau to zero.

As used herein, a "waveform" can refer to a graphical representation of changes in current or voltage over time.

As used herein, the term "hyperpolarization block" can refer to the cessation of nerve signaling in one or more nerves within target neural tissue caused by the accumulation of negative charges and/or loss of positive charges within a cell, lowering its membrane potential below its resting potential. For example, an influx of negative chloride ions or a loss of positive potassium ions can prevent the activation gates of voltage-gated sodium channels from opening, making action potentials more difficult to generate. An anodic (negatively charged) current can be used to cause a hyperpolarization block.

As used herein, the term "depolarization block" can refer to the cessation of nerve signaling in one or more nerves within target neural tissue caused by the accumulation of certain positively charged ions within a cell. For example, increased intracellular potassium ion levels can close inactivation gates in voltage-gated sodium channels within the cellular membrane, such that the movement of sodium into the cell is reduced and action potentials are inhibited. A cathodic (positively charged) current can be used to cause a depolarization block.

As used herein, the term "polarity" can refer to a direction of electron movement. For example, the polarity can be cathodic (positively charged) or anodic (negatively charged).

As used herein, the terms "reversed polarity" and "reverse polarity" can refer to a switch in the direction of electron movement. For example, an anodic current (negatively charged) is of reversed polarity from a cathodic (positively charged) current, and vice versa.

As used herein, the term "nerve" can refer to at least one or more fibers (e.g. axons) of nerve cells that employ electrical and chemical signals to transmit motor, sensory, and/or autonomic information from one body part to another. A nerve can refer to a component of the central nervous system and/or the peripheral nervous system. Additionally, one or more nerves can make up neural tissue.

As used herein, the term "recovery" can refer to the re-establishment of normal signaling/activation patterns in a nerve after disruption.

As used herein, the term "recovery time" can refer to an amount of time required for normal signaling/activation patterns to return after a period of disruption.

As used herein, the terms "nerve activity" and "neural activity" can refer to signaling (conduction) and activation patterns to transmit neural signals carrying neural information.

As used herein, the term "conduction" can refer to movement of charged particles through space (e.g., a nerve fiber), forming an electrical current. Electrical block can be used to attenuate conduction through one or more nerves.

As used herein, the term "amplitude" can refer to a measurement of the dependent variable (e.g., current, voltage, etc.) above or below zero.

As used herein, the term "threshold" can refer to a stimulus amplitude generally required to produce a complete nerve block.

As used herein, the term "sub-threshold" can refer to a stimulus with an amplitude that is below that which is typically required to produce a complete nerve block.

As used herein, the term "electrode" can refer to a material acting as a conductor through which electricity enters or leaves. At least a portion of the material can be a biocompatible material. An example of an electrode that can be used to deliver electrical nerve block is a separated interface nerve electrode (SINE), in which the electrode is separated from a nerve interface by a column of electrolyte, providing a less harmful way to deliver the electrical block. However, different types of electrodes can be used and are not limited to the SINE.

As used herein, the term "enhance" can refer to intensify, increase, or improve the quality, value, or extent of something.

As used herein, the terms "subject" and "patient" can be used interchangeably and refer to any warm-blooded organism including, but not limited to, a human being, a pig, a rat, a mouse, a dog, a cat, a goat, a sheep, a horse, a monkey, an ape, a rabbit, a cow, etc.

II. Overview

Direct current (DC) can be applied to a nerve to generate a complete nerve block. A problem with applying DC to the nerve with a traditional electrode is the generation of reaction products, which can damage the nerve. Newer electrodes, such as the separated interface nerve electrode (SINE), are designed to reduce or eliminate the damaging effects of the irreversible reaction products when the DC is applied to the nerve. When DC is applied for a prolonged period of time with these newer electrodes, such as the SINE, however, a delay is seen in the reversibility of the block and recovery of the neural response, requiring a substantial recovery period. The recovery period can be reduced by applying a repolarizing waveform (e.g., a subthreshold DC of the opposite polarity) after application of the DC at or above the block threshold.

Accordingly, the present disclosure is related to the accelerated recovery from direct current (DC) nerve block using repolarization. Specifically, the systems and methods described herein can be used to accelerate the recovery of nerve conduction post-block by applying a sub-threshold reversed-polarity DC waveform to the nerve. Additionally, changing the electric field caused by the sub-threshold reversed-polarity DC waveform enhances nerve conduction, even when applied alone and/or when the nerve is still blocked. Using the systems and methods of the present disclosure, nerve block can be administered to a patient, completely numbing some portion of the patient's body when needed, for example, and the numbing can be reversed instantaneously (or at least nearly immediately with a reduced response time).

III. Systems

An aspect of the present disclosure can include a system 10 (FIG. 1) that can be used to achieve accelerated recovery from direct current (DC) nerve block using repolarization. DC can be applied to a nerve to generate a complete nerve block (e.g., with an anodic or cathodic amplitude at or above the threshold for block). Newer electrodes, like the separated interface nerve electrode (SINE), have been designed to reduce or eliminate the damaging consequences of irreversible reaction products. Accordingly, the newer electrodes allow DC block to be administered for a prolonged period of time, but when the DC is applied for a prolonged period of time, however, a delay is seen in the reversibility of the block and recovery of the neural response, requiring a substantial recovery period. The system 10 can reduce the recovery period by applying a repolarizing waveform (e.g., a subthreshold DC of the opposite polarity—anodic if the block is cathodic, cathodic if the block is anodic). As a practical example, using the system 10, nerve block can be administered to a patient, completely numbing some portion of the patient's body when needed, for example, and the numbing can be reversed instantaneously (or at least nearly immediately with a reduced response time). Additionally, the reverse polarity waveform applied by the system 10 can enhance neural activity, even when applied alone and/or when the nerve is still blocked.

The system 10 includes at least one or more electrodes (shown as electrode 12, but it will be understood that the electrodes are not restricted to a single device) and one or more waveform generators (shown as current generator 14, but it will be understood that the waveform generator is not restricted to only a single device that only generates current). The one or more electrodes (including electrode 12) can be coupled to the current generator 14 for signal transmission therebetween. The coupling can be a wireless coupling, a wired coupling, or a combination of wired coupling and wireless coupling. As an example, the coupling can be a wired coupling so that a signal can be transmitted between the current generator 14 and the electrode 12.

The current generator 14 can be configured or programmed to generate the electrical signal, for example a DC, configured with an amplitude sufficient to cause block in at least a portion of neural tissue (e.g., sensory neurons, motor neurons, autonomic neurons, enteric neurons, interneurons, central nervous system neurons, etc.). Accordingly, the current generator 14 can be any device configured or programmed to generate the specified electrical signal. One example of a current generator 14 is a battery-powered, portable generator. Another example of a current generator 14 is an implantable generator (IPG). It will be appreciated that the current generator 14 can include additional components to selectively configure the current waveform, such as an amplitude modulator (not shown). As an example, the current generator 14 can be configured or programmed to generate a DC waveform having monophasic waveform or a biphasic waveform, with one phase cathodic and one anodic. As another example, the current generator 14 can be configured or programmed to generate a charge balance polarizing current (CBPC) waveform.

In some instances, the generated DC waveform can have an anodic polarity or a cathodic polarity, and an amplitude sufficient to cause the DC block. For block, the DC can have an amplitude that is at least a block threshold. The block threshold for different types of nerves of different sizes may be different. The DC used for block can be cathodic (positively charged) with a cathodic amplitude of at least the cathodic block threshold or anodic (negatively charged) with an anodic amplitude of at least the anodic block threshold. The DC block can be provided as hyperpolarization block or depolarization block. Hyperpolarization block is caused by the accumulation of negative charges and/or loss of positive charges within a cell, lowering its membrane potential below its resting potential, caused by an anodic current. Depolarizing block is caused by the accumulation of certain positively charged ions within a cell, caused by a cathodic current. The DC used for block can be administered for a time. As a non-limiting example, the time can be more than 2 minutes. As another non-limiting example, the time can be more than 5 minutes. As yet another non-limiting example, the time can be more than 10 minutes.

The electrode 12 can be configured to deliver the electrical signal to neural tissue. For example, the electrode 12 can be coupled to the current generator 14 to receive the electrical signal and deliver the electrical signal to the neural tissue to provide the block for the time. The electrode 12 can be a newer electrode design, which can be designed to avoid irreversible Faradaic reactions, like hydrogen evolution, oxygen evolution, chlorine evolution, or the like, at the high DC charge required to deliver the nerve block. For example, the electrode 12 can use a separated interface, separating the electrode and the nerve. As another example, the electrode 12 can utilize high capacitance electrode materials and/or high charge capacity electrode materials. Specific examples of electrodes that can be used as the electrode 12 include a separated interface nerve electrode (SINE), a carbon coated platinum electrode, a woven cloth carbon electrode, a carbon slurry electrode, or the like (e.g., designed as described in at least one of U.S. Pat. Nos. 9,008,800, 9,496,621, WO 2019/133783, WO 2019/133784, U.S. Pat. No. 9,387,322, or U.S. Pat. No. 10,195,434, which are incorporated herein by reference).

After the time, the current generator 14 can be configured or programmed to generate another electrical signal with another amplitude (different from the amplitude of the original electrical signal) for another time. The other electrical signal can be a DC or a CBDC, configured with the other amplitude that is sub-threshold (i.e., does not cause block in at least a portion of neural tissue) and of the opposite polarity (also referred to as reversed polarity) from that of the originally generated DC waveform. In other words, the other amplitude can be of the reversed polarity than the amplitude of the originally generated DC waveform. For example, if the original DC waveform has an anodic polarity, the other electrical signal can have a cathodic polarity. Similarly, if the original DC waveform has a cathodic polarity, the other electrical signal can have an anodic polarity.

The sub-threshold amplitude can be any value less than the threshold (e.g., either the cathodic threshold or the anodic threshold, depending on the polarity of the other electrical signal). For example, the sub-threshold amplitude can be from 0.1% of the threshold to 99.9% of the threshold. As another example, the sub-threshold amplitude can be a value less than 85% of the threshold. As further example, the sub-threshold amplitude can be a value less than 50% of the threshold. As yet another example, the sub-threshold amplitude can be a value less than 30% of the threshold. It should be noted that the value of the sub-threshold amplitude may be based on the type of nerve and/or the location of the nerve. For example, a smaller nerve may require a different amplitude value than a larger nerve.

The electrode 12 can receive the other electrical signal from the current generator 14 and deliver the other electrical signal to the neural tissue for the other time. The other signal can cause the one or more nerves within the neural tissue to enter a repolarization cycle to accelerate the recovery from the block (in other words, accelerate recovery time for the nerve). In some instances, neural activity can be fully restored in the nerve after the second time.

The recovery time can be markedly reduced when the sub-threshold, reversed polarity DC is applied. It should be understood that the recovery time can be reduced to be less than it would be with application of the DC signal without the other DC signal. In some instances, the recovery time can be from 10 minutes to about 0 seconds (nearly instantaneous). For example, the recovery time for the nerve can be less than 1000 s. As another example, the recovery time for the nerve can be less than 500 s. As a further example, the recovery time for the nerve can be less than 250 s. The recovery time may be based on the type of nerve and/or the location of the nerve. For example, a smaller nerve may require a different recovery time than a larger nerve.

The reversed polarity, sub-threshold other electrical signal can preserve the reversibility of DC nerve block when the DC nerve block is applied for a prolonged period of time. Using the reversed polarity, sub-threshold other electrical signal can be used, for example, when a DC nerve block is delivered to provide complete numbing of a portion of a patient's body, using the reversed polarity, sub-threshold other electrical signal can ensure that it is always known that the numbing can be reversed whenever it is desired.

Additionally, applying an electrical signal, either for block or repolarization, can change the electrical field in proximity to the nerve. When the blocking electrical signal is applied, the electric field can change to block the neural activity (e.g., conduction). When the sub-threshold electrical signal is applied, the electric field can change to one that provides a positive effect on nerve conduction. In some instances, application of the sub-threshold electrical signal can have an enhancement effect on neural activity, including nerve conduction. The sub-threshold electrical signal, in some instances, can have an enhancement effect on neural activity when applied by itself without blocking. The sub-threshold electrical signal, in other instances, can have an enhancement effect on neural activity when applied in conduction with a blocking electrical signal. The sub-threshold electrical signal, in still other instances, can have an enhancement effect on neural activity when applied after application of a blocking signal.

Figure 2:
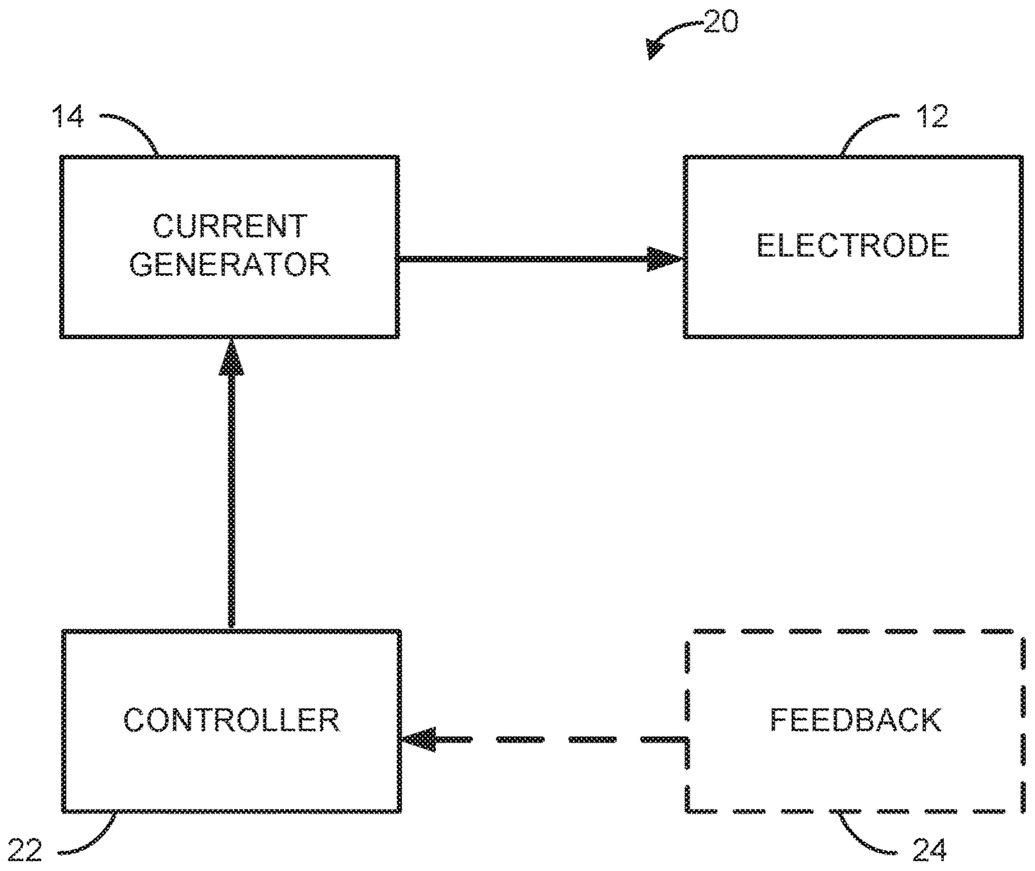
FIG. 2 shows an example of the system of claim 1 with the waveform generator receiving input from a controller.

As shown in FIG. 2, the current generator 14 can be coupled to one or more controllers (shown as a single controller 22 in FIG. 2). The controller(s) 22 can be implantable and/or external. The controller(s) 22 can be configured to set one or more parameters of the electrical signal and/or the other electrical signal delivered by the current generator 14. The parameters can include polarity, amplitude, timing, and the like, for the electrical signal and/or the other electrical signal. It should be noted that one or more of the parameters will be different for each of the electrical signal and the other electrical signal.

In some instances, the controller(s) 22 can be programmed with set values for the one or more parameters of the electrical signal and/or the other electrical signal. In other instances, the controller(s) 22 can alter a value of the one or more parameters based on feedback 24. For example, the feedback 24 can be a user input (in this example, the controller 22 can have safety concerns programmed therein to prevent the one or more parameters to be adjusted to an unsafe or ineffective level). As another example, the feedback 24 can be from a sensor within the subject's body either before delivery of the electrical signal and the other electrical signal or after delivery of the electrical signal.

For example, the controller(s) 22 can be configured to program the current generator to generate the electrical signal with an amplitude and a polarity for a first time. The amplitude can be at least a threshold value (to provide block) and the polarity can be either anodic or cathodic. These parameters can be pre-programmed into the controller 22 or set according to a user input. The controller 22 can also be configured to program the current generator to generate the electrical signal with another amplitude and a reverse polarity for a second time. The other amplitude can be less than a threshold value (so not to provide block) and the polarity can be the reverse of that of the electrical signal—e.g., if the polarity of the electrical signal is either anodic or cathodic, the polarity of the other electrical signal is either cathodic or anodic. These parameters can be pre-programmed into the controller 22 or set according to a user input. For example, the amplitudes, polarities, and/or time of application of the electrical signal and/or the other electrical signal can be preprogrammed into the controller, but the start time of application of the other electrical signal can be set according to a user input.

IV. Methods

Figure 3:
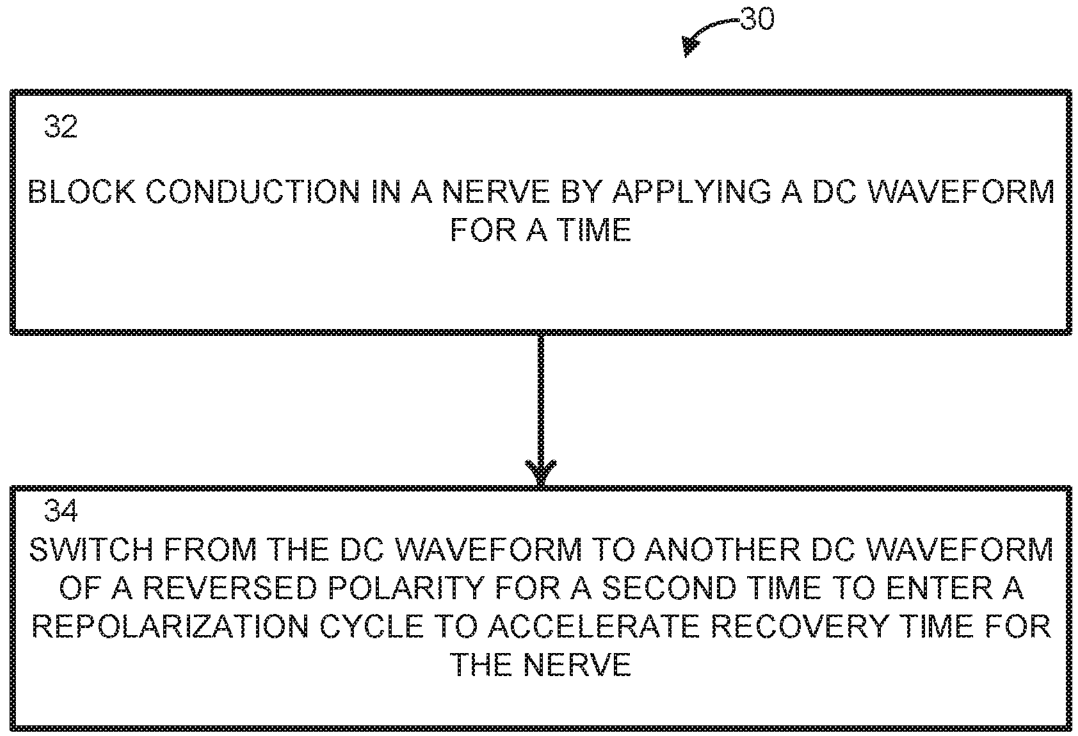
FIG. 3 is a process flow diagram illustrating a method for accelerating recovery from DC nerve block using repolarization in accordance with another aspect of the present disclosure.
Figure 4:
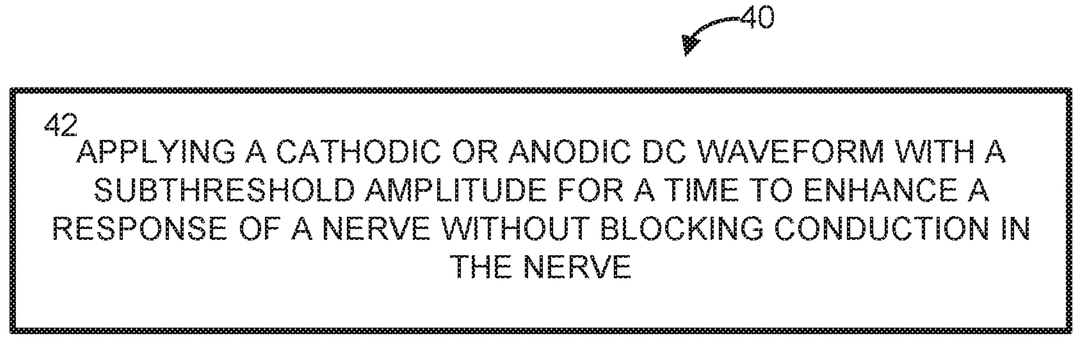
FIG. 4 is a process flow diagram illustrating a method for enhancing a response of the nerve without blocking conduction in the nerve in accordance with yet another aspect of the present disclosure.

Another aspect of the present disclosure can include methods 30 and 40 for achieving the effects of applying a repolarization DC current to a nerve, as shown in FIGS. 3 and 4. The methods 30 and 40 can be executed using the systems 10 or 20 shown in FIGS. 1 and 2, using the electrode(s) 12 designed to avoid Faradaic reactions, like hydrogen evolution, oxygen evolution, chlorine evolution, or the like, when delivering a large charge to neural tissue. For example, the electrode(s) 12 can utilize a saline interface. As another example, the electrode(s) 12 can utilize high capacitance electrode materials. Specific examples of electrodes that can be used as the electrode(s) 12 include a separated interface nerve electrode (SINE), a carbon coated platinum electrode, a woven cloth carbon electrode, a carbon slurry electrode, or the like.

For purposes of simplicity, the methods 30 and 40 are shown and described as being executed serially; however, it is to be understood and appreciated that the present disclosure is not limited by the illustrated order as some steps could occur in different orders and/or concurrently with other steps shown and described herein. Moreover, not all illustrated aspects may be required to implement the methods 30 and 40.

Referring now to FIG. 3, illustrated is an example of a method 30 for accelerating recovery from DC nerve block using repolarization. The reversed polarity, sub-threshold other electrical signal can preserve the reversibility of DC nerve block when the DC nerve block is applied for a prolonged period of time. At Step 32, conduction in a nerve (or general neural activity) can be blocked by applying a DC waveform for a time (e.g., a DC or a CBDC generated by current generator 14 and applied by electrode 12). The DC waveform can have an amplitude of at least a block threshold. At Step 34, the DC waveform can be switched (e.g., according to controller 22) to another DC waveform of a reversed polarity for a second time (e.g., a DC or a CBDC generated by current generator 14 and applied by electrode 12) to enter a repolarization cycle to accelerate recovery time for the nerve. The other DC waveform can be a sub-threshold DC waveform of the reversed polarity that does not cause block.

The sub-threshold amplitude can be any value less than the threshold (e.g., either the cathodic threshold or the anodic threshold, depending on the polarity of the other electrical signal). For example, the sub-threshold amplitude can be from 0.1% of the threshold to 99.9% of the threshold. As another example, the sub-threshold amplitude can be a value less than 85% of the threshold. As further example, the sub-threshold amplitude can be a value less than 50% of the threshold. As yet another example, the sub-threshold amplitude can be a value less than 30% of the threshold. It should be noted that the value of the sub-threshold amplitude may be based on the type of nerve and/or the location of the nerve. For example, a smaller nerve may require a different amplitude value than a larger nerve.

The recovery time can be markedly reduced when the sub-threshold, reversed polarity DC is applied. It should be understood that the recovery time can be reduced to be less than it would be with application of the DC signal without the other DC signal. In some instances, the recovery time can be from 10 minutes to about 0 seconds (nearly instantaneous). For example, the recovery time for the nerve can be less than 1000 s. As another example, the recovery time for the nerve can be less than 500 s. As a further example, the recovery time for the nerve can be less than 250 s. The recovery time may be based on the type of nerve and/or the location of the nerve. For example, a smaller nerve may require a different recovery time than a larger nerve.

Referring now to FIG. 4, illustrated is another example of a method 40 for enhancing a response of the nerve using repolarization without blocking conduction in the nerve. At Step 42, a cathodic or anodic DC waveform with a sub-threshold amplitude can be applied for a time to enhance a response of a nerve without blocking conduction in the nerve. The response of the nerve can be, for example, conduction.

Applying an electrical signal, either for block or repolarization, can change the electrical field in proximity to the nerve. When the blocking electrical signal is applied, the electric field can change to block the neural activity (e.g., conduction). When the sub-threshold electrical signal is applied, the electric field can change to one that provides a positive effect on nerve conduction. In some instances, application of the sub-threshold electrical signal can have an enhancement effect on neural activity, including nerve conduction. The sub-threshold electrical signal, in some instances, can have an enhancement effect on neural activity when applied by itself without blocking. The sub-threshold electrical signal, in other instances, can have an enhancement effect on neural activity when applied in conduction with a blocking electrical signal. The sub-threshold electrical signal, in still other instances, can have an enhancement effect on neural activity when applied after application of a blocking signal.

V. Examples

The following example describes procedure and results showing accelerated recovery of direct current (DC) blocking using repolarization. The following example is for the purpose of illustration only is not intended to limit the scope of the appended claims.

Methods

SINE Electrode Setup

Figure 5:
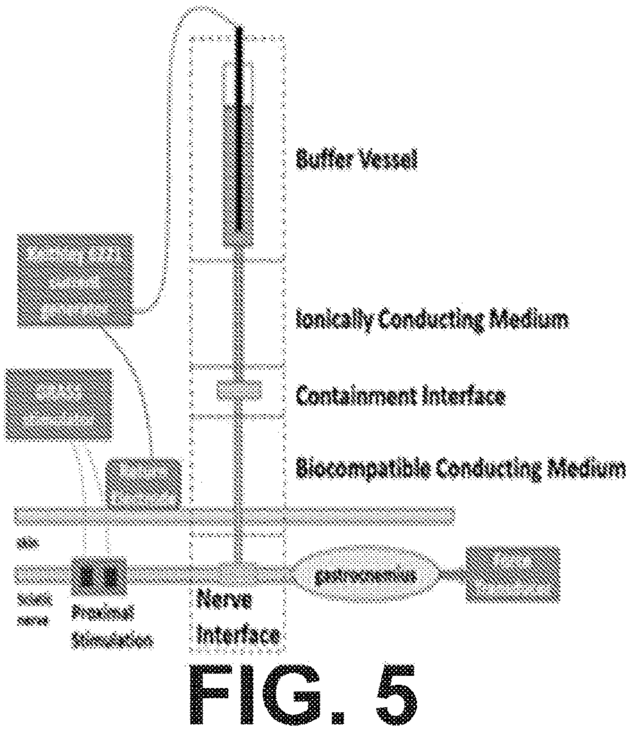
FIG. 5 shows an experimental set-up using a separated interface nerve electrode (SINE)

An acute experiment was conducted on one adult male rat 491 g (Sprague-Dawley), under institutional approval. The animal was anaesthetized with inhaled Isoflurane to effect. A SINE electrode was used for conduction block. To improve charge capacity, the vessel was filled with a high surface area carbon/saline "slurry". The metal electrode and the nerve cuff interface were physically separated with a column of electrolyte. Any reactions that occur at the metal electrode were contained in the electrolyte. To improve the capacity of the SINE electrode, high surface area carbon (YP-50, Kuraray, Canoga Park, CA, USA) was added to the saline to form a stiff paste. The carbon paste that was used to fill this buffer consisted of 3 g of carbon to 7 g of electrolyte (0.9 wt % saline). In this embodiment, a corrosion resistant graphite rod was used as the electrode contact. A syringe filter separated the carbon slurry from the biocompatible conducting medium, preventing the carbon from leaching down to the nerve. A silicone cuff was fabricated in house using silicone tubing to interface with the nerve. The cuff helps to hold the electrode in place close to the nerve. A current-controlled constant current generator (Keithley, Inc.) was used to provide both the depolarization and the repolarization cycles. A proximal stimulation electrode was placed proximally on the sciatic nerve to elicit muscle contractions from the gastrocnemius. Muscle contractions were measured by attaching the Achilles tendon to a force transducer. Proximal stimulation was provided by a Grass S88 Grass Technologies, West Warwick, RI, USA) stimulator through a voltage to current isolator at levels that produced a maximum muscle twitch (1 Hz, 20 μS, and 0.4-1 mA). The blocking electrode was applied 10 mm distally through a separate incision and the return was a hypodermic needle placed subcutaneously on top of the biceps femoris muscle. An example preparation of the SINE electrode is shown in FIG. 5.

In Vivo Testing

Block threshold was defined as the lowest value at which complete block occurred within 30 s of application. The block thresholds using both a cathodic (negative) current and anodic (positive) current were determined.

Once the block thresholds were determined, the recovery time for complete block using the cathodic current was measured. The current was applied at the cathodic block threshold for 10 minutes. After 10 minutes, the current was turned off and the time for the force to completely recover was determined.

After the recovery time for complete block was determined, the accelerated recovery time was tested using various time periods of repolarization. First the current output was set to the block threshold for the cathodic current for 10 minutes of block. The output was then transitioned to 25% of the anodic block current for one of three time periods (90, 120, and 200 s). After this time period the block was turned off. The recovery time for the force was then recorded.

Results

Block Threshold

Figure 6:
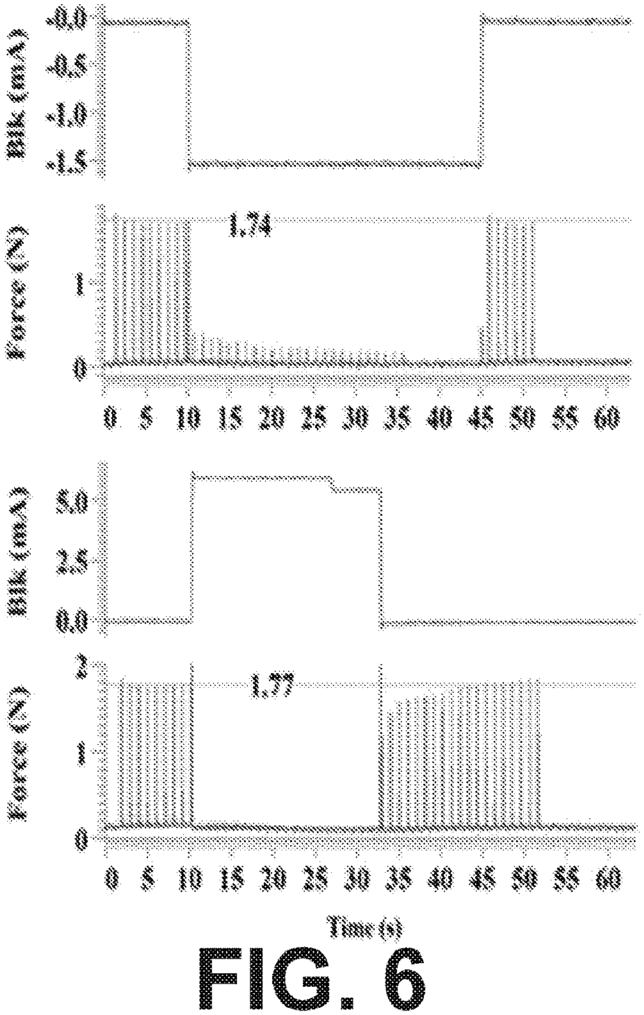
FIG. 6 shows examples of cathodic (top) and anodic (bottom) block, illustrating that both cathodic and anodic currents can cause block, but block thresholds are lower for cathodic.

The negative polarity block threshold was determined to be −1.5 mA and the positive block threshold was determined to be +6.0 mA. FIG. 6 shows the complete block of force for values of −1.5 mA (top) and +6.0 mA (bottom). For the experiment, 25% of positive block threshold (1.5 mA) was used to test recovery acceleration.

Test with No Recovery Acceleration

Figure 7:
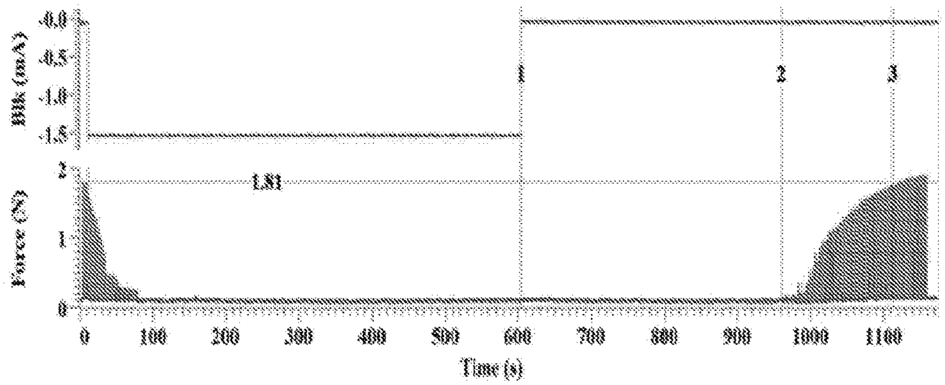
FIG. 7 shows an example of recovery from complete cathodic block without recovery acceleration.

As shown in FIG. 7, complete block was achieved 60 s after application of a −1.5 mA DC block. After 10 minutes, recovery was monitored. Recovery of force twitches was achieved 357 s after the block was removed and complete force recovery occurred after an additional 152 s for a total recovery time of 509 s.

Test with Recovery Acceleration

Figure 8:
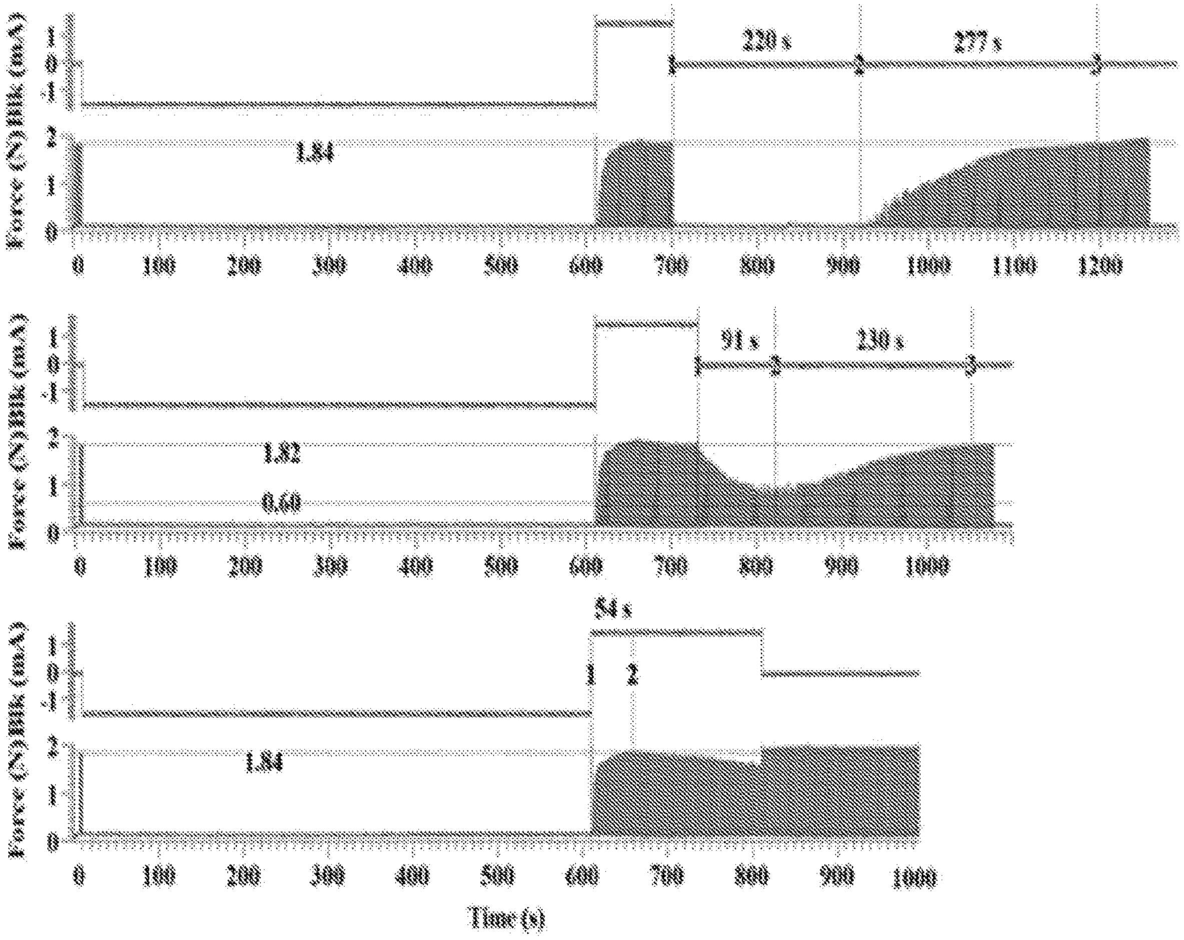
FIG. 8 shows examples of recovery from complete cathodic block with recovery acceleration.

In FIG. 8, recovery acceleration is shown for repolarization periods of 90 s (top of FIG. 8), 120 s (middle of FIG. 8), and 200 s (bottom of FIG. 8). For the 90 s trial, force recovery occurred immediately, but then was reduced to 0 N when the DC was removed (0 mA). Initial force twitches can be seen DC was 220 s after the DC is removed with an additional 277 s for full force recovery. To determine the recovery times from the end of the 10 minutes of total block, the amount of time of repolarization (90 s) needs to be added for a twitch recovery for a twitch recovery time of 310 s and a full force recovery of 587 s.

For the 120 s trial, the force recovery is maintained after the DC is removed, but decays, and then eventually recovers. The twitch recovery after the removal of DC was 91 s with an additional 230 s for full force recovery. To determine the recovery times from the end of the 10 minutes' total block period, the amount of time of repolarization (120 s) needs to be added for a twitch recovery of 211 s and a full force recovery of 441 s.

For the 200 s trial, the repolarization phase actually starts to cause a conduction block (force reduction) after 54 s, and then complete recovery happens immediately when the DC is removed. In this example, sustained full force recovery occurs immediately after the repolarization interval for a full force recovery time of 200 s.

From the above description, those skilled in the art will perceive improvements, changes and modifications. Such improvements, changes and modifications are within the skill of one in the art and are intended to be covered by the appended claims.

The following is claimed:

1. A method comprising:

blocking conduction in a nerve by applying a DC waveform to the nerve for a first time with at least one electrode contact in electrical communication with the nerve, wherein the DC waveform has a polarity with an amplitude that is a magnitude above a block threshold of the nerve for the polarity, wherein applying the DC waveform with the at least one electrode for the first time is configured to create a hyperpolarization block or a depolarization block of the nerve, and wherein the first time is two minutes or more; and switching from applying the DC waveform to applying another DC waveform with the at least one electrode contact for a second time, after the first time, to force the nerve to enter a repolarization cycle to accelerate a recovery time for the nerve to return to a normal neural response when the second time is ended, wherein the other DC waveform has an opposite polarity with another amplitude that is a magnitude below a block threshold of the nerve for the opposite polarity, and wherein applying the other DC waveform with the at least one electrode contact for the second time depolarizes the hyperpolarization block or hyperpolarizes the depolarization block to bring a membrane potential of the nerve back to a resting potential of the nerve.

2. The method of claim 1, wherein the recovery time for the nerve is less than 1000 s.

3. The method of claim 1, wherein the recovery time for the nerve is less than 500 s.

4. The method of claim 1, wherein the recovery time for the nerve is less than 250 s.

5. The method of claim 1, wherein the other amplitude is a magnitude less than 85% of the block threshold of the nerve for the opposite polarity.

6. The method of claim 1, wherein the other amplitude is a magnitude less than 50% of the block threshold of the nerve for the opposite polarity.

7. The method of claim 1, wherein the other amplitude is a magnitude less than 30% of the block threshold of the nerve for the opposite polarity.

8. The method of claim 1, wherein the nerve comprises at least two fiber types and wherein one of the at least two fiber types has a faster speed of recovery than another of the at least two fiber types.

9. The method of claim 1, wherein conduction in the nerve is fully restored after the second time.

10. A system comprising:

a current generator;

a controller in communication with the current generator and programmed to instruct the current generator:

generate a DC waveform of a polarity with an amplitude that is a magnitude above a block threshold for a nerve for the polarity for a first time, wherein the first time is two minutes or more; and after the first time, generate another DC waveform with an opposite polarity and another amplitude for a second time, after the first time, wherein the other amplitude is a magnitude below the block threshold of the nerve for the opposite polarity; and at least one electrode contact, coupled to the current generator and configured to be in electrical communication with the nerve, the controller further programmed instruct the current generator to:

apply the DC waveform to the nerve, via the at least one electrode contact, to block conduction in the nerve for the first time to create a hyperpolarization block or a depolarization block of the nerve, and then switch from application of the DC waveform to apply the other DC waveform to the nerve, via the at least one electrode contact, for the second time, after the first time to force the nerve to enter a repolarization cycle to accelerate a recovery time for the nerve to return to a normal neural response when the second time is ended, wherein application of the other DC waveform for the second time depolarizes the hyperpolarization block or hyperpolarizes the depolarization block to bring a membrane potential of the nerve back to a resting potential of the nerve.

11. The system of claim 10, wherein conduction in the nerve is fully restored after the second time.

12. The system of claim 10, wherein the other amplitude is a magnitude less than 85% of the threshold of the nerve for the opposite polarity.

13. The system of claim 10, wherein the other amplitude is a magnitude less than 50% of the threshold of the nerve for the opposite polarity.

* * * * *